United States Patent
Gardner

(10) Patent No.: US 9,418,204 B2
(45) Date of Patent: Aug. 16, 2016

(54) BIOINFORMATICS SYSTEM ARCHITECTURE WITH DATA AND PROCESS INTEGRATION

(75) Inventor: Steve Gardner, Royston (GB)

(73) Assignee: Samsung Electronics Co., Ltd (KR)

( * ) Notice: Subject to any disclaimer, the term of this patent is extended or adjusted under 35 U.S.C. 154(b) by 1421 days.

(21) Appl. No.: 11/613,112

(22) Filed: Dec. 19, 2006

(65) Prior Publication Data

US 2008/0033999 A1      Feb. 7, 2008

Related U.S. Application Data

(63) Continuation of application No. 10/352,246, filed on Jan. 28, 2003, now abandoned.

(60) Provisional application No. 60/351,378, filed on Jan. 28, 2002, provisional application No. 60/351,379, filed on Jan. 28, 2002, provisional application No. 60/351,380, filed on Jan. 28, 2002, provisional application No. 60/366,236, filed on Mar. 22, 2002.

(51) Int. Cl.
*G06F 17/30* (2006.01)
*G06F 19/26* (2011.01)
*G06F 19/28* (2011.01)

(52) U.S. Cl.
CPC ............... *G06F 19/26* (2013.01); *G06F 19/28* (2013.01)

(58) Field of Classification Search
CPC .......... G06F 17/30; G06F 19/28; G06F 19/26
USPC ................................................... 707/3, 707
See application file for complete search history.

(56) References Cited

U.S. PATENT DOCUMENTS 5,953,727 A    9/1999    Maslyn et al.
5,966,712 A    10/1999   Sabatini et al.
(Continued)

FOREIGN PATENT DOCUMENTS

WO    01/15042    3/2001
WO    02/10980    2/2002

OTHER PUBLICATIONS

Goble, Professor Carole, "Supporting Web Based Biology with Ontologies", Information Technology Applications in Biomedicine, Oct. 9-10, 2000; pp. 384-389.
(Continued)

*Primary Examiner* — Vincent Boccio
(74) *Attorney, Agent, or Firm* — The Farrell Law Firm, P.C.

(57) ABSTRACT

A bioinformatics system and method is provided for integrated processing of biological data. According to one embodiment, the invention provides an interlocking series of target identification, target validation, lead identification, and lead optimization modules in a discovery platform oriented around specific components of the drug discovery process. The discovery platform of the invention utilizes genomic, proteomic, and other biological data stored in structured as well as unstructured databases. According to another embodiment, the invention provides overall platform/architecture with integration approach for searching and processing the data stored in the structured as well as unstructured databases. According to another embodiment, the invention provides a user interface, affording users the ability to access and process tasks for the drug discovery process.

22 Claims, 13 Drawing Sheets

310 Control Panel
312 Data Source Portion
314 Processes Portion
316 Results Portion
318 Agents Portion
320 Object Buttons
325 Explorer Panel
330 Alternate Display View
335 Data Source Selection
340 Search Dialog Box 150 User Interface

(56) References Cited

U.S. PATENT DOCUMENTS

| | | | |
|---|---|---|---|
| 5,970,500 | A | 10/1999 | Sabatini et al. |
| 6,023,659 | A | 2/2000 | Seilhamer et al. |
| 6,125,383 | A | 9/2000 | Glynias et al. |
| 6,185,561 | B1 | 2/2001 | Balaban et al. |
| 6,189,013 | B1 | 2/2001 | Maslyn et al. |
| 6,223,186 | B1 | 4/2001 | Rigault et al. |
| 6,229,911 | B1 | 5/2001 | Balaban et al. |
| 6,263,287 | B1 | 7/2001 | Zheng et al. |
| 6,904,428 | B2 * | 6/2005 | Frieder et al. |
| 6,920,396 | B1 * | 7/2005 | Wallace et al. ............... 702/19 |
| 6,941,317 | B1 * | 9/2005 | Chamberlin et al. ......... 707/102 |
| 7,076,484 | B2 * | 7/2006 | Dworkis et al. ................. 707/5 |
| 7,133,864 | B2 * | 11/2006 | Roth .............................. 707/3 |
| 7,139,755 | B2 * | 11/2006 | Hammond ....................... 707/5 |
| 7,194,483 | B1 * | 3/2007 | Mohan et al. ............. 707/104.1 |
| 7,231,390 | B2 * | 6/2007 | Blair et al. ....................... 707/6 |
| 7,349,811 | B2 * | 3/2008 | Bulla, Jr. et al. ............... 702/19 |
| 7,536,413 | B1 * | 5/2009 | Mohan et al. ............. 707/103 R |
| 2001/0032210 | A1 * | 10/2001 | Frank et al. ............... 707/104.1 |
| 2001/0037332 | A1 * | 11/2001 | Miller et al. ..................... 707/4 |
| 2001/0047353 | A1 * | 11/2001 | Talib et al. ....................... 707/3 |
| 2002/0055932 | A1 * | 5/2002 | Wheeler et al. ........... 707/104.1 |
| 2002/0067358 | A1 * | 6/2002 | Casari et al. ................. 345/440 |
| 2002/0133504 | A1 * | 9/2002 | Vlahos et al. ............. 707/104.1 |
| 2002/0156771 | A1 * | 10/2002 | Frieder et al. ..................... 707/3 |
| 2002/0169764 | A1 * | 11/2002 | Kincaid et al. .................... 707/3 |
| 2002/0194154 | A1 * | 12/2002 | Levy et al. ......................... 707/1 |
| 2003/0028501 | A1 * | 2/2003 | Balaban et al. ................... 707/1 |
| 2003/0055835 | A1 * | 3/2003 | Roth ............................ 707/102 |
| 2003/0176929 | A1 * | 9/2003 | Gardner ......................... 700/17 |
| 2004/0230572 | A1 * | 11/2004 | Omoigui ........................... 707/3 |
| 2006/0064415 | A1 * | 3/2006 | Guyon et al. ..................... 707/6 |

OTHER PUBLICATIONS

Baker, Patricia G., et al, "An Ontology for Bioinformatics Applications", Bioinformatics, vol. 15, No. 6, Jun. 1999, pp. 510-520.

Goble, C.A., et al., "Transparent Access to Multiple Bioinformatics Information Sources", IBM Systems Journal, vol. 40, No. 2, 2001, pp. 532-551.

Lambrix, Patrick, et al., "Evaluation of Ontology Development Tools for Bioinformatics", Bioinformatics, vol. 19, No. 12, 2003, pp. 1564-1571.

Hwang, Chung Hee, "Incompletely and Imprecisely Speaking: Using Dynamic Ontologies for Representing and Retrieving Information", Microelectronics and Computer Technology Corporation, © 1999, 4 pages.

Eckman et al., Bioinformatics, vol. 17, 2001, pp. 587-601.

* cited by examiner

150 User Interface
310 Control Panel
312 Data Source Portion
314 Processes Portion
316 Results Portion
318 Agents Portion
320 Object Buttons
325 Explorer Panel
330 Alternate Display View
335 Data Source Selection
340 Search Dialog Box 410 Results Table
415 Selection Field
420 Type Field
425 Database Field
430 Name Field
435 Description Field

BIOINFORMATICS SYSTEM ARCHITECTURE WITH DATA AND PROCESS INTEGRATION

CROSS-REFERENCE TO RELATED APPLICATIONS

This application is a continuation of co-pending U.S. patent application Ser. No. 10/352,246, filed Jan. 28, 2003, and claims priority to U.S. Provisional Patent Application Ser. No. 60/351,378, filed Jan. 28, 2002, U.S. Provisional Patent Application Ser. No. 60/351,379, filed Jan. 28, 2002, U.S. Provisional Patent Application Ser. No. 60/351,380, filed Jan. 28, 2002, and U.S. Provisional Patent Application Ser. No. 60/366,236, filed on Mar. 22, 2002, each of which are incorporated by reference in their entirety.

The following U.S. Patent Applications, filed contemporaneously herewith, are specifically and entirely incorporated herein by reference: U.S. patent application Ser. No. 10/352, 242, filed Jan. 28, 2003, titled "Modular Bioinformatics Platform;" U.S. patent application Ser. No. 10/352,196, filed Jan. 28, 2003, titled "User Interface for a Bioinformatics System;" U.S. patent application Ser. No. 10/352,197, filed Jan. 28, 2003, titled "Ontology-Based Information Management System and Method."

FIELD OF THE INVENTION

The invention relates to a system and method for integrating numerous and diverse data sources, data processing and decision support tools to facilitate overall portfolio management for life science related industries.

BACKGROUND OF THE INVENTION

The life sciences are undergoing a paradigm shift from a traditional laboratory (wet science) driven industry to a truly information-driven industry. A new understanding of the workings of life at the genetic and molecular levels, together with laboratory automation, promises to make the processes associated with finding new drugs, therapies, and agricultural products radically faster, cheaper, and more effective. As a result, a formidable volume of data are pouring out of innovative technologies such as genomics, combinatorial chemistry, and high-throughput screening at an unprecedented rate.

The challenges that accompany the management of massive volumes of data may be compounded by the fact that life sciences data are often dispersed throughout the research and development (R&D) enterprise, across the public domain, and within the labs of external research partners. The data, which tends to be highly complex and constantly changing, may often be stored in multiple heterogeneous formats such as 3-D chemical structure databases, relational database tables, flat files, text stores, image repositories, web sources and other formats. This data may further reside on different hardware platforms, under different operating systems, and in different database management systems.

The lack of structure in some data sources, or the use of differing structures amongst structured data sources, also presents challenges to those trying to process the diverse sources. Unstructured data sources often store data as strings of data (e.g. text of a journal article) which makes it difficult to ascertain the relevance of a particular piece of the data when read out of context. For example, a text search for the string "alanine" in an unstructured database may retrieve a document where "alanine" is present in a single footnote and a document where "alanine" is discussed in depth. In an unstructured database, it may be difficult to differentiate between the documents.

Another challenge that arises from the volume of information currently inundating researchers is that it may be difficult to make intelligent decisions regarding particular avenues of research and development to pursue. For example, a company may be developing several promising new drugs, each at a different stage of regulatory approval processes, it would be profitable for the company to be able to make informed decisions regarding how to allocate company resources to maximize the overall revenue given the current state of the company's drug portfolio. Existing systems do not provide tools to facilitate such decisions.

Many pharmaceutical and biotechnology companies have recognized that the information challenge they face may consist largely of inefficiencies with existing information technology (IT) systems. As a result, many of these institutions have increased spending on IT research and development. Unfortunately, many drawbacks remain as the new technologies that have been adopted generally focus on optimizing particular tasks within the data management process, rather than focusing on the optimization of the data management process itself These and other drawbacks exist.

SUMMARY OF THE INVENTION

In order to overcome these and other drawbacks of existing systems, the present invention provides an integrated system of data resources, informatics tools, user interfaces and other services.

Some embodiments of the system enable scientists and other researchers to access the data resources, operate on the data with the informatics tools and access other services and functions, all through a relatively intuitive user interface.

One advantage of the invention is that it provides life scientists, and other researchers, with access to timely information on their desktops.

Another advantage of the invention is that it provides for accelerated and accurate decision making by providing the user with relatively easy access to decision enabling tools and information.

Another advantage of the invention is that it provides improved information flow and removes many information flow bottlenecks.

Another advantage of the invention is that it facilitates information sharing on multidisciplinary projects and between multidisciplinary teams.

Another advantage of the invention is that it enhances research and development productivity by providing automated analysis and report generation tools.

Another advantage of the invention is that it implements technology components that are well understood in the field and enables rapid acclimatization for users.

In order to accomplish these and other advantages of the invention, there is provided an integrated informatics platform that enables access to genetic, protein, chemical, biological, scientific literature, patent, textual, and other data sources and enables integrated cross referencing and data manipulation to extract information and generate reports.

The following example demonstrates some advantages of the invention when the invention is implemented for bioinformatics applications. While the context of this example is life sciences, it is understood that the invention is not so limited. Other research and informatic applications are possible.

The study of the life sciences encompasses many disciplines. For example, medicine, pharmacology, genetics, proteomics, chemistry, and other disciplines all fall under the umbrella of life sciences.

Data that is collected and published for each of these disciplines may comprise many formats and structures. Some of the formats are structured (e.g., the GENBANK™ database of gene expressions) and some are unstructured (e.g., the database of articles published in the journal "Nature"). The diversity of formats increases the difficulty of data extraction across multiple data sources.

The present invention provides an integrated approach to data access that enables greater ease of data extraction across multiple data sources. One aspect of the data integration is enabled by providing a data warehouse of suitably cleaned and parsed structured data formats. For example, the system may obtain data from various structured data sources (e.g., EMBL, Ensembl, KEGG, NCI_60, etc.), and parse, cleanse and load the data into a data warehouse.

A user that searches the data in the data warehouse is able to access the data from each data source (e.g., EMBL, Ensembl, KEGG, NCI_60, etc.) without format concerns.

Another aspect of the data integration is to provide access to unstructured data sources (e.g., Thompson's databases of textual information) along side of the access to structured data sources. The unstructured data sources may be accessed through appropriate modules that categorize and retrieve the textual data (e.g., via Smartlogik processing).

Still another aspect of data integration afforded by the invention is that it enables integration of the underlying processes. For example, a researcher may identify a number of promising gene targets that may influence a certain medical condition (e.g. pancreatic cancer), the invention enables the researcher to take the identified gene targets and input them into additional data sources (e.g., a proteomics database) to extract additional information that may influence the research project (e.g., the proteins and enzymes that influence the target genes). Additional levels of integration, such as extracting the metabolic pathways influenced by the identified proteins and enzymes, are also possible.

Still another aspect of the integration afforded by the invention is that it enables business processes to be correlated to the more traditional research processes. For example, the invention enables projected costs and revenues to be factored into the data analysis tools.

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

FIG. 15 illustrates a search dialog according to one embodiment of the invention.

DETAILED DESCRIPTION OF PREFERRED EMBODIMENTS

The following examples illustrate some of the integration enabled by the invention. In one scenario, a research project may use the invention to cross-correlate gene location, metabolic pathway function, expression profile and sequence attributes all from the researcher's desktop. Using the provided analysis tools, the researcher may analyze and cluster the data to identify the most promising genes. Following that, and still at the desktop, the researcher may be able to identify all of the patents and scientific papers related to the identified genes. The researcher then may be able to analyze the costs of continuing research on the identified genes.

Alternatively, a researcher may come across a patent or scientific article of interest and use that information as input into the system. The invention categorizes the information, identifies gene based concepts and searches for the gene based concepts in the structured data sources. Once located, the gene expression properties may be correlated. Finally, research and other (e.g., FDA approval) costs may be factored in and analyzed to evaluate the benefits of developing a research project based on the identified genes.

Figure 1:
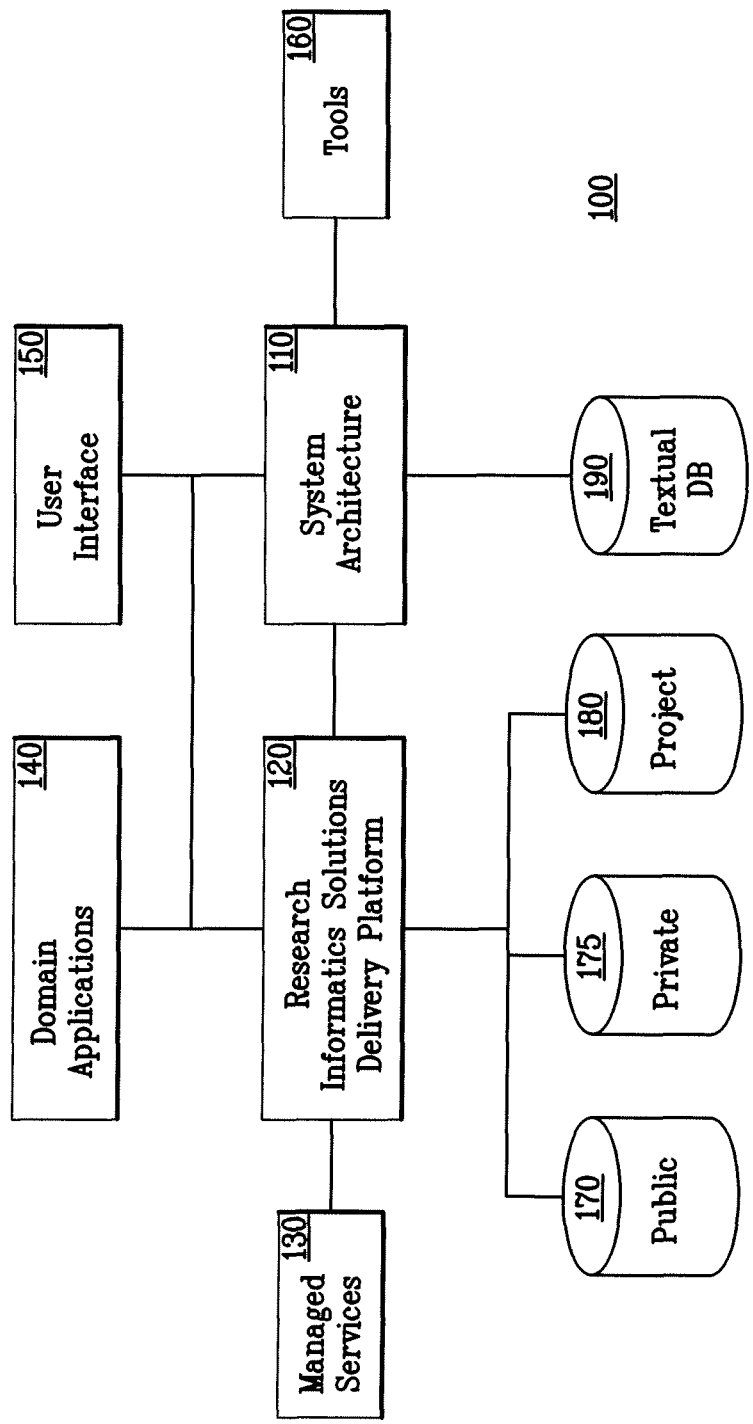
FIG. 1 illustrates an exemplary bioinformatics system according to one embodiment of the invention.

FIG. 1 illustrates an exemplary embodiment of the present invention. According to the present invention, a bioinformatics system 100 interfaces to one or more research informatics solutions delivery platforms 120, one or more domain applications 140, a user interface 150, and a tool set 160. Bioinformatics system 100 may also be coupled to a textual database via various known mechanisms. As illustrated in FIG. 1, RIS 120 may also be coupled to one or more managed services 130 as well as various data sources including one or more public databases 170, one or more private databases 175, and one or more project databases 180, again via various known mechanisms. Each of these components are described in further detail below.

Figure 2:
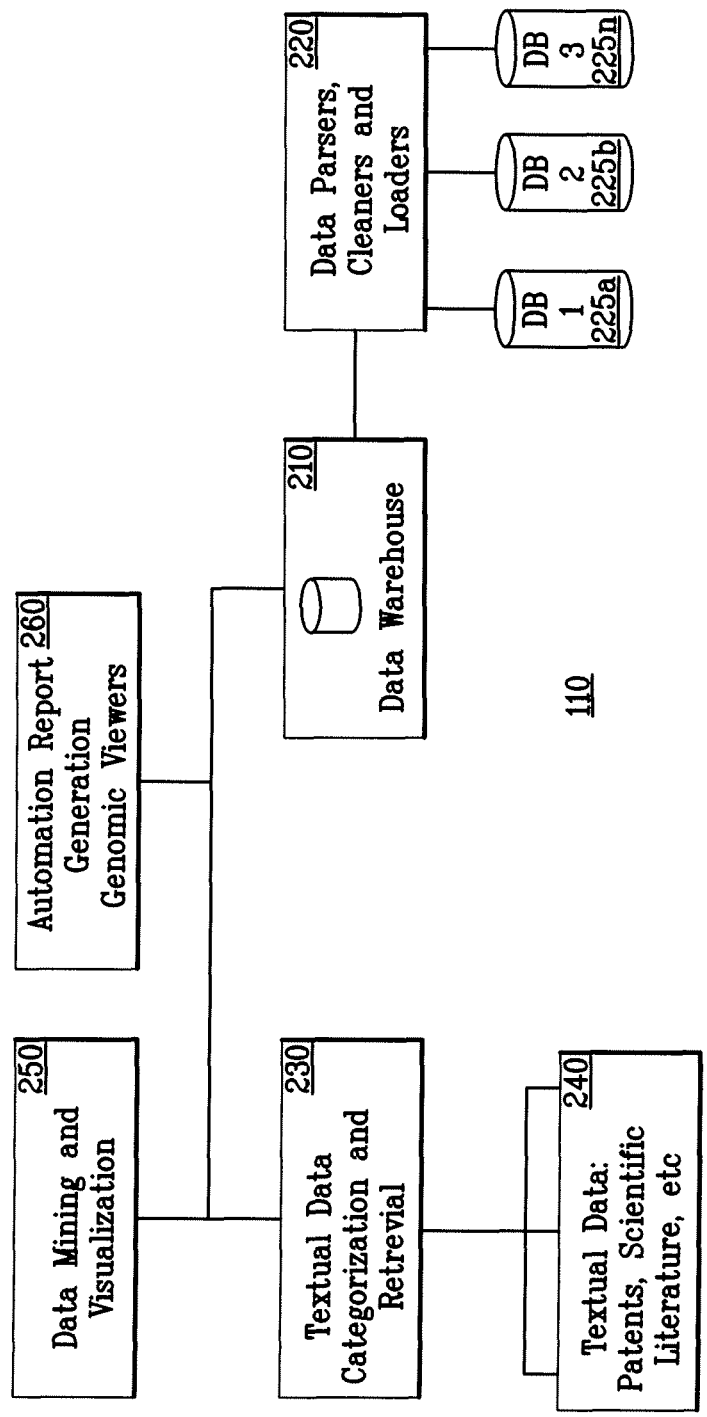
FIG. 2 illustrates a functional block diagram of a bioinformatics system according to one or more embodiments of the invention.

FIG. 2 illustrates a functional block diagram of bioinformatics system 100 according to one or more embodiments of the invention. As illustrated, bioinformatics system 100 may include a data warehouse 210 for storing various data including various bioinformatics data. Data warehouse 210 functions as a central repository for this data once it is gathered by bioinformatics system 100. Data warehouse 210 may be coupled to one or more data parsers, data cleaners, and/or data loaders (hereinafter referred to collectively as data parsers 220). In some embodiments of the invention, data parsers 220 are used to import data from disparate databases 225 (illustrated as a database 225A, a database 225B, and a database 225N) of different origin and transform the content included therein into a common format for processing by bioinformatics system 100. A unique data parser 220 may be used for each type of database 225 as would be apparent. Data parsers 220 allow data to be retrieved from database 225 and utilized by bioinformatics system 100 as would be apparent.

Data warehouse 210 may be coupled to a textual data module 230 that in turn is coupled to one or more textual data stores 240 including, but not limited to, patent data, scientific data, scientific literature, or other form of textual or unstructured data. Textual data module 230 may be used to categorize and retrieve unstructured data in a form useful for combining with other data sources including structured data sources. In general, textual data modules 230 are known and may include one or more commercially available tools from, for example, Smartlogik.

Data warehouse 210 may also be coupled to one or more data mining and/or visualization modules 250 that are useful for accessing, retrieving and presenting information included in for example, textual data stores 240. In general, data mining and visualization modules 150 are known and may include one or more commercially available tools from, for example, Inforsense. Data warehouse 210 may also be coupled to one or more report generators and/or genomic viewers 260 that are useful for consolidating, organizing and/or presenting information included in for example, textual data stores 240. In general, report generators and/or genomic viewers 260 are known and may include one or more commercially available tools from, for example, Inforsense.

As illustrated in FIG. 1 and FIG. 2, bioinformatics system 100 provides access to a number of data resources (e.g., public databases 170, private databases 175, project databases 180, textual data stores 240 and other databases or sources of information). Bioinformatics system 100 also provides access to a number of informatics tools (e.g., data mining and visualization tools 250, workflow and automation tools 260, decision support tools, report generation 260 and other informatics tools). Bioinformatics system 100 may also provide access to research informatics solution platforms 120 and other managed services 130 (e.g., research informatics applications, on-line storage, high performance computing, systems monitoring, and customer support).

According to one aspect of the invention, bioinformatics system 100 provides an intuitive browser-enabled user interface 150 that provides a user with access to the system. User interface 150 may include a graphical user interface (GUI). The user interface 150 enables navigation throughout the system and enables the user to prepare and execute searches, obtain and analyze the results, and/or visualize and display the results.

In some embodiments of the invention, user interface 150 is browser enabled although other any suitable GUI may be used. In some embodiments o the invention, user interface 150 may be created using hyper text markup language (HTML). Java applets may also be used for one or more visualization (or other) displays. Those having skill in the art should recognize, however, that any suitable text markup language including any one or more of, for instance, XML, TCL, Visual Basic, or ActiveX may also be usable within, or in conjunction with, the browser-enabled user interface system.

In some embodiments of the invention, user interface 150 may include one or more panels, windows, or frames (collectively, "panels") for navigating through various research processes in accordance with the invention. Each panel may comprise a number of selection portions, including, but not limited to, tabs, buttons, pull-down menus, scroll bars, check boxes, hypertext links, hot links, or other known navigational that enable users to select, access, display, or navigate through various charts, graphs, spreadsheets, displays, search forms, data fields, or other information associated with bioinformatics system 100.

Figure 3:
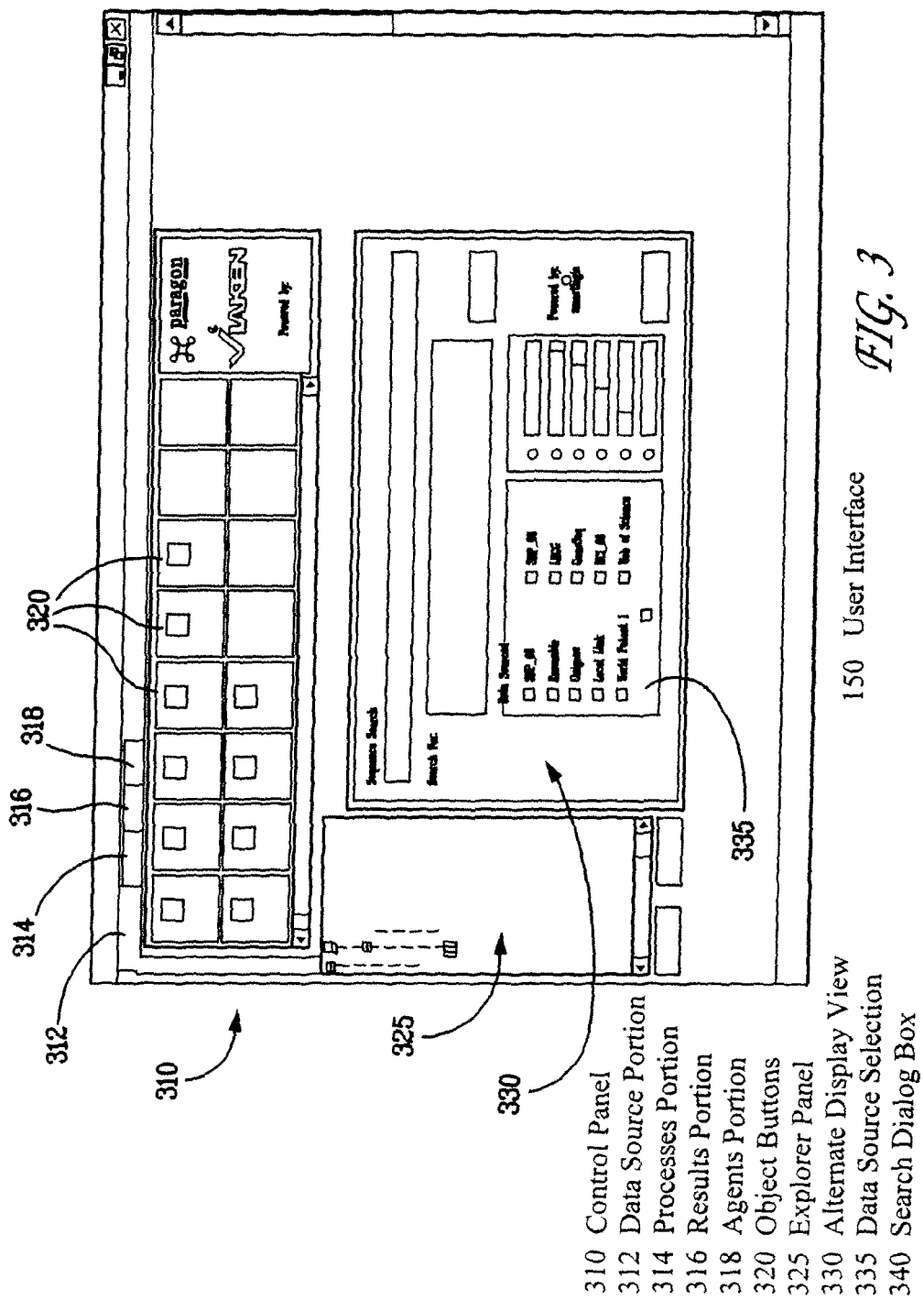
FIG. 3 illustrates a user interface according to an embodiment of the invention.

In one embodiment of the invention, such as that illustrated in FIG. 3, user interface 150 includes a control panel portion 310, an explorer panel 325, and a display panel 330. Control panel 310 provides access to the various data sources and processes, which may be vary according to the intended application. According to an embodiment of the invention, control panel 310 may serve as the primary navigation panel for the user interface. Control panel 310 may include a series of tabs that provide an overall control of workflow. A series of buttons associated with each tab may be selected by the user to provide access to various data sources and processes, which may be customized. Each tab, button, or other selection portion may comprise a logo, text, or any icon, symbol, or graphic identifying the function of the selection portion to a user.

Selecting a tab may result in the display of a list of buttons, each of which may represent an available relevant object. Generally, the selection of a button by a user may result in the display of a view in the display panel. Various views including, for example, search forms, search results, and visualization tools (e.g., charts, graphs, or other data displays) may be displayed in the display panel.

In one embodiment of the invention, control panel 310 includes separate portions (i.e., tabs or other selection mechanism) such as a data source portion 312 to access various data sources, a process portion 314 to access various processes, a results portion 316 to access various results, and an agents portion 318 to access various agents. As would be apparent, other portions may be provided.

Each portion included in control panel 310 may include one or more objects (such as objects 320 for data source portion 312 illustrated in FIG. 3) relevant to that portion. The relevant objects displayed within a given portion may vary according to its context (e.g., if a series of DNA sequences have been returned by a search, only those processes that accept DNA sequences as input might be displayed within process portion 314).

In some embodiments, accessing a portion in control panel 310 may create a new view in a display panel 330. The new view may include objects such as data preparation (search), results, and visualization tools.

Access to objects within a given portion may be accomplished in any suitable fashion. For example, graphical icons (e.g., buttons) and textual descriptions (e.g., names) may be provided to access objects.

Figure 5:
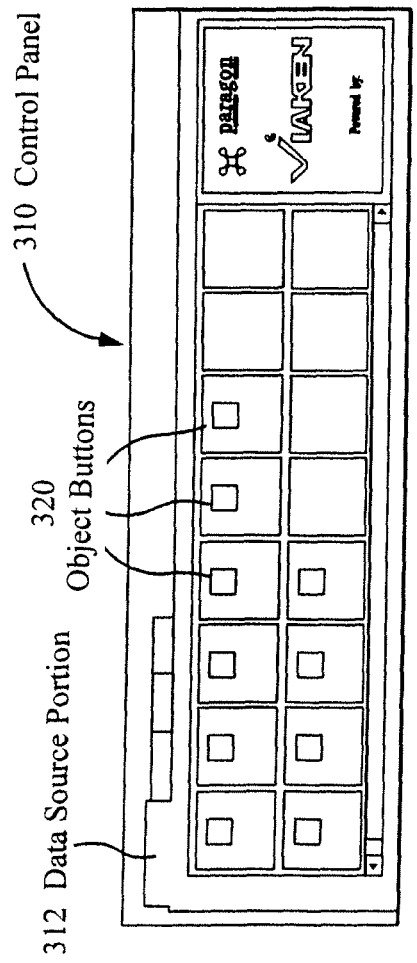
FIG. 5 illustrates a view of a control panel when a data sources portion is selected in accordance with one embodiment of the invention.

In some embodiments of the invention, when the user selects data source portion 312 in control panel 310, the user may be presented with one or more buttons that each correspond to various types of data that may be accessed by bioinformatics system 100. These buttons allow users select the type of data against which the user wishes to run a particular process. The user selects the type of data to be retrieved including sequence data, expression data, locus data, cluster data, pathway data, gene data, scientific literature data, patent data, project data, text data, and other types of data. Such a selection may be enabled, for example as illustrated in FIG. 5, via various buttons 320 in control panel 310 including, for example, a sequence button, expression button, locus button, cluster button, pathway button, gene button, scientific literature button, patent button, project button, and text button, as illustrated, as well as other buttons for other types of data.

According to an embodiment of the invention, once a type of data is selected by the user, various sources 335 for that type of data may be presented to the user. These data sources may comprise one or more public, private, or commercial databases, including, for example, Genbank or RMBL, Unigene, SNP DB, Ensembl, or KEGG (Pathways and Annotations), as well as one or more textual databases such as Derwent GENESEQ, Derwent GENESEQ FASTALert, Derwent World Patents Index, Derwent World Drug Index, Derwent Drug File, Derwent World Drug Alerts, Derwent Gene Therapy Database, Derwent Biotechnology Abstracts, Derwent Pharma PatentSource, Medline, ISI Web of Science, or Current Contents Life Sciences. Other data sources may be accessed by the invention as would be apparent. In some embodiments of the invention, the data sources presented to the user may or may not depend on the type of data selected.

One advantage of selecting a data type from data sources portion 312 of the control panel 310 is that it enables different source and types of data to be correlated that might otherwise be overlooked. For example, a user searching metabolic pathway data in the KEGG database may also get related sequence objects returned to run an SNP analysis against. In conventional systems, the only practical way to bring back sequence data was to run queries against sequence databases in which case, a scientist could potentially miss an interesting sequence that is referenced in the KEGG database related to, for example, bronchial asthma.

Upon selecting a button that represents a desired type of data, a view including the appropriate search dialogs for the selected data type may then be displayed in a display panel. For example, an appropriate search dialog 340 for the selected data type may be displayed in a display panel 330 of user interface 150. Some search dialogs for extracting information from the various data sources may be common to all data sources and some search dialogs may vary according to the data source as would be apparent.

The view in the display panel 330 may also include one or more tabs (representing available search dialogs) that enable a user to select how the various data sources may be queried. Examples of search dialogs may include, but are not limited to the following: Boolean text searching, expression pattern searching, similarity searching, and other types of search dialogs. Additional searching tools, such as BLAST, FASTA, and Smith-Waterman may also be made available to users.

As illustrated in FIG. 15, probabilistic text searching may provide users with the ability to drop entire documents into a search engine 1510 through, for example, a browse mechanism 1515. Such tools are commercially available from, for example, Smartlogik. In addition, the user may, for example, be presented with one or more data sources 1520 to search against, as well as options 1530 for selecting a statistical relevance of any keywords used in the search.

Boolean text searching may be selected by users seeking a more granular searching mechanism. This searching mechanism may, in certain embodiments, include several fields for narrowing or focusing a search. An additional "find-related" selection portion may, when selected, enable users to engage in probabilistic searching for a particular field within the Boolean search. Users may be able to search by various fields including, but not limited to, accession, author, base count, comment, cross reference, date of last update, description, division, EC number, features, feature key, full text, gene name, journal name, keywords, locus, medline, organism, reference title, sequence length, and version. Various qualifiers may be selected by users when structuring a search, including, for example, "contains all of" "contains any of," "contains phrase," "does NOT contain," "less than," and "greater than."

It should be recognized, however, that the searching methods made available to a user in the display panel may differ based on which of the buttons (representing different types of data) has been selected from the list of buttons under the data sources tab. According to an embodiment of the invention, for example, probabilistic text searching may be made available to users regardless of which button (or type of data) is selected, while boolean text searching and searching using the BLAST, FASTA, and Smith-Waterman tools may vary with each button (type of data) selected. For example, users selecting sequence data, expression data, and gene buttons may employ any of the searching tools offered, while users selecting the locus, cluster, pathway, scientific literature, patent, project, and text buttons may, for example, be presented with the option to use only probabilistic text searching and/or boolean text searching.

After selecting one or more data sources from the list of data sources 335 and executing a search within search dialog 340, user interface 150 may display the results of the search. The results may be displayed in an appropriate manner. For example, the results may be displayed automatically in display portion 330 of user interface 150 as, for example, as a table, chart, or other graphic representation.

Figure 4:
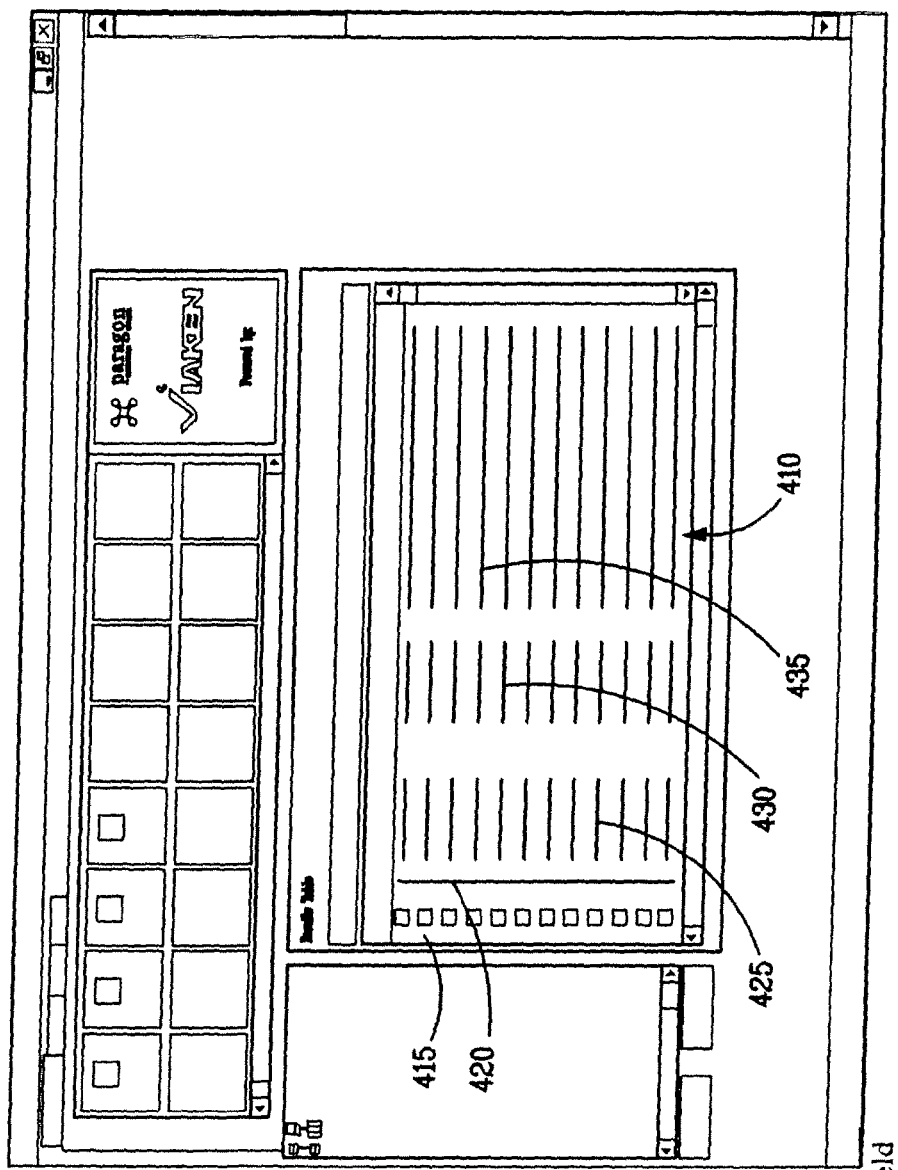
FIG. 4 illustrates an exemplary results table according to one aspect of the invention.

FIG. 4 illustrates an exemplary results table 410 according to one aspect of the invention. The results table may have a number of fields including a selection field 415, a type field 420, a database field 425, a name field 430, a description field 435, etc. Selection field 415 may enable a user to select the various results (e.g. through a check box) for which additional actions may be performed (e.g., an iterative query or subsequent process).

Type field 420 may graphically represent the type of object associated with the underlying result and/or may identify further actions that may be taken (e.g., the process or iterative query).

Database field 425 may display the data source from which the underlying result was extracted. For example, sequence data could have been extracted from the Kegg database.

Name field 430 identifies the underlying result. For example, for sequence data results, the name field may include an accession number.

Description field 435 describes the underlying result. The description field may vary with the type of data as would be apparent. Description field may include, or be otherwise associated with, a link to where the result may be displayed in its common format (e.g., using Bio Java).

Figure 13:
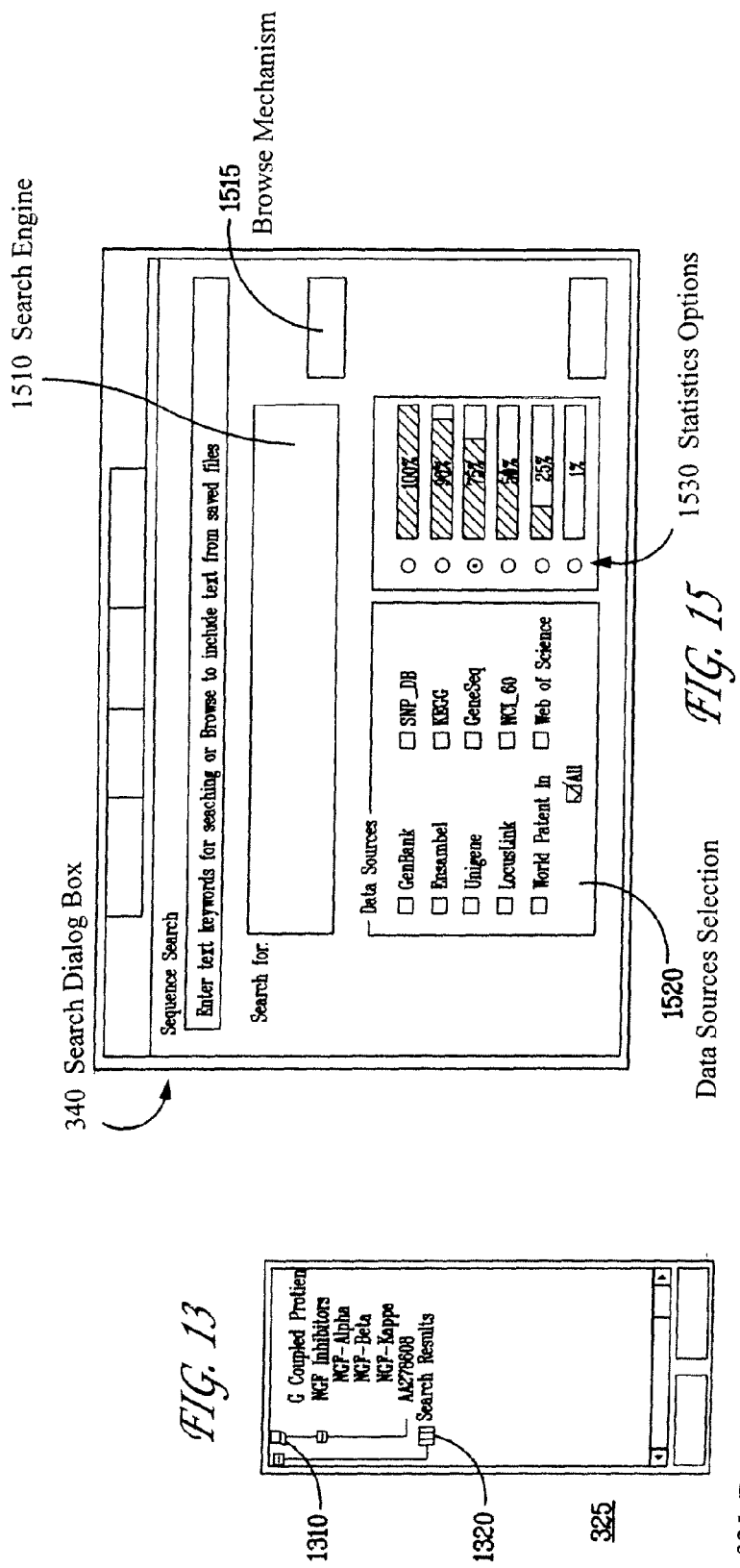
FIG. 13 illustrates an explorer panel including a hierarchal representation of the results according to one embodiment of the invention.

In some embodiments, in addition to the results displayed in display portion 330, an item may appear in the explorer panel 325 that represents that data set. In one embodiment, this item may appear as a hierarchal representation 1310 of the results in explorer panel 325 of user interface 150 such as illustrated in FIG. 13. For example, explorer panel 325 may display hierarchal representation 1310 including steps taken to execute the search (e.g., project title, data source selected, search dialog, search results, etc.). The results may be displayed in explorer panel 325 by a representation 1320 (e.g., an icon) of that data set. Representation 1320 of the search results may be persistent for a given session but do not have to remain when a new session is started. In addition, representation 1320 may be graphically linked to the types of processes that can be run against those search results as well as the data source icons.

After viewing the results in results table 410, a user may desire to perform additional processes or additional searching. According to one aspect of the invention, bioinformatics system 100 enables the user to iteratively query data sources to return additional data including other types of data related to the initial query. This option may be available via as a process icon selectable within process portion 314 or other selection portion as would be apparent. Upon electing an iterative query, the user may be represented with data source portion 312 to run the query against another data source. For example, a user may run a probabilistic text search for asthma across Kegg and GenBank data sources, which may return sequence objects having a 75% relevance. Next, the user may select (e.g., from the result table in display panel 330) five entries from the Kegg data source and two entries from the GenBank data source to run an additional query against and activate the iterative query. The user is then presented with one or more of the data sources against which to run the selected results. The user again has a choice of relevance, data source and type of data returned. Following through with this example, the user may choose to run the previously selected results against NCI-60 with a 50% relevance thereby retrieving related expression results. The user may repeat the iterative process as desired or choose to move on to process the search results.

Once the data is prepared for running against a process, one or more business or research processes may be displayed in control panel 310. Some examples of these processes may include, but are not limited to, cluster sequencing, threading, SNP analysis, expression, protein alignment, HTS searching, align reference sequence, cluster references, cluster patents, and other processes.

In some embodiments of the invention, the user may select a processes portion 314 of control panel 310 which causes the display of various buttons 320 associated with the processes (i.e., "process objects") that are available for users of bioinformatics system 100. These buttons may include, for example, a cluster sequences button, a threading button, an SNP analysis button, an expression button, a protein atigr button, an HTS search button, an align reference sequence button, a cluster references button, and cluster patents button. Other buttons may be used as would be apparent.

In some embodiments of the invention, these process objects may represent Kensington taskgraphs and may have been generated in a number of ways. Other commercially available processes or algorithms may be used as would be apparent. Furthermore, additional processes may be configured to operate with bioinformatics system 100 as would also be apparent. In general, the process objects may comprise standard pieces of bioinformatics system 100, functionality developed by third parties, custom pieces provided by request, or customizations generated by the users.

In some embodiments of the invention, only those processes relevant to the type of data in the search results are displayed in control panel 310 when processes portion 314 is selected. For example, in the above example, only those buttons associated with processes capable of receiving and processing expression data will be displayed for search results including expression data and those buttons associated with processes capable of receiving and processing sequence data will be displayed for search results including DNA sequences.

Figure 6:
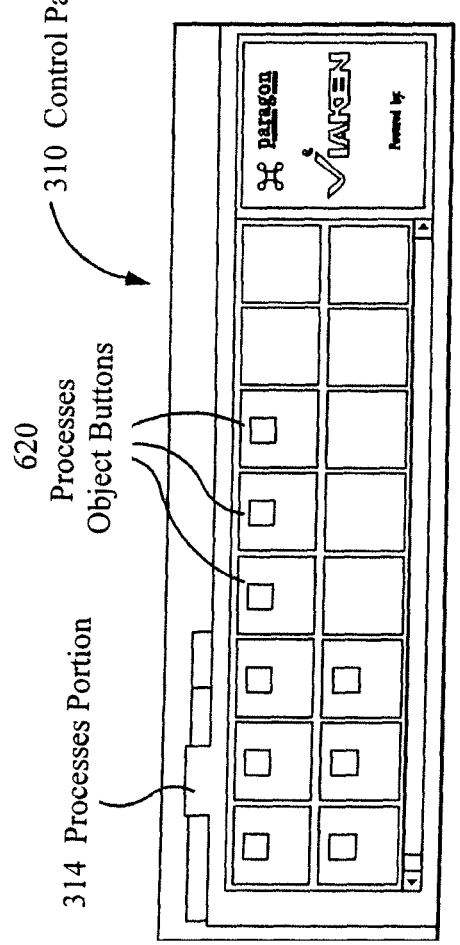
FIG. 6 illustrates a view of a control panel when a processes portion is selected in accordance with one embodiment of the invention.

The process buttons may be represented using a graphical icon and textual description or name such as, for example, buttons 620 in control panel 310 illustrated in FIG. 6. For example, the process buttons may have two graphics representing input and output data types as well as a brief textual identifier. The process buttons may also be linked to various help items. For example, if the button is right clicked, the display may show some annotation associated with the associated process object for reference by the user.

In some embodiments of the invention, user interface 150 may enable users to create detailed informatics workflows and place them as buttons with titles and icons in user interface 150.

After the user selects one of process buttons 620, the associated process object processes the selected data and returns the results of that processing which are displayed using an appropriate results viewer in display panel 330. A corresponding process result may also appear in explorer panel 325 under the associated data querying result.

In some embodiments, the results view may be displayed automatically upon completion of the processing. In other embodiments, the results view may be displayed by the user selecting results portion 316 in control panel 310. The results may be displayed in any suitable manner. For example, a results table or a visual interface in the form of a Java applet from Kensington. In addition, some embodiments of the invention may enable users to create and store custom informatics workflow processes.

Examples of results viewers may include, but are not limited to, a table viewer, a text/XML viewer, a decision tree browser, an interactive data browser, a 3D aggregate data browser, a visual clustering browser, a rule browser, a dendogram browser, a 2D/3D scatterplot, a 2D/3D histogram, and a 2D/3D pie chart, as well as a multiple sequence alignment viewer, and/or a sequence similarity results viewer. Other results viewers may also be enabled. The results viewers may, in some embodiments, comprise viewers provided by a third party service provider.

Figure 7:
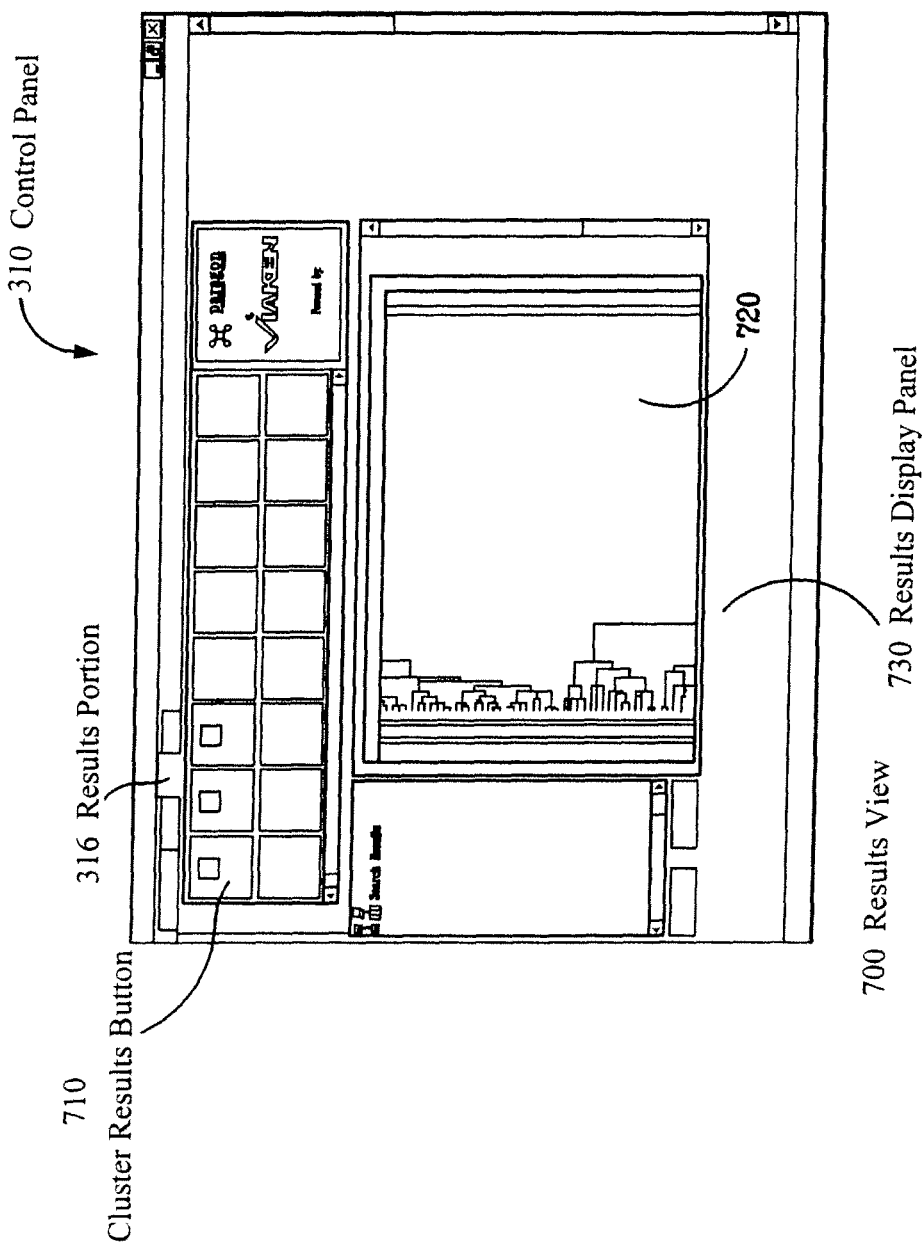
FIG. 7 illustrates a results view associated with cluster results in a display panel according to one embodiment of the invention.
Figure 8:
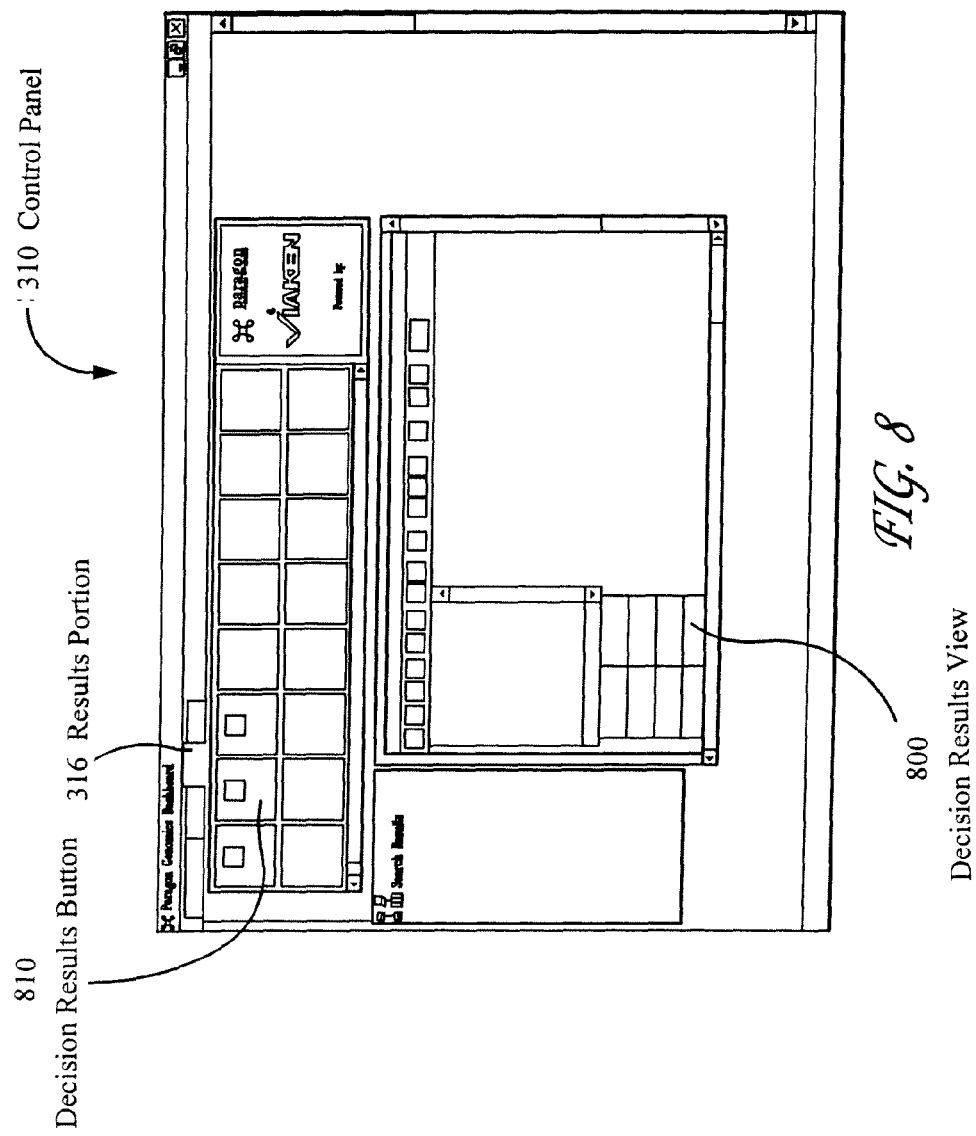
FIG. 8 illustrates a results view associated with decision results in a display panel according to one embodiment of the invention.
Figure 9:
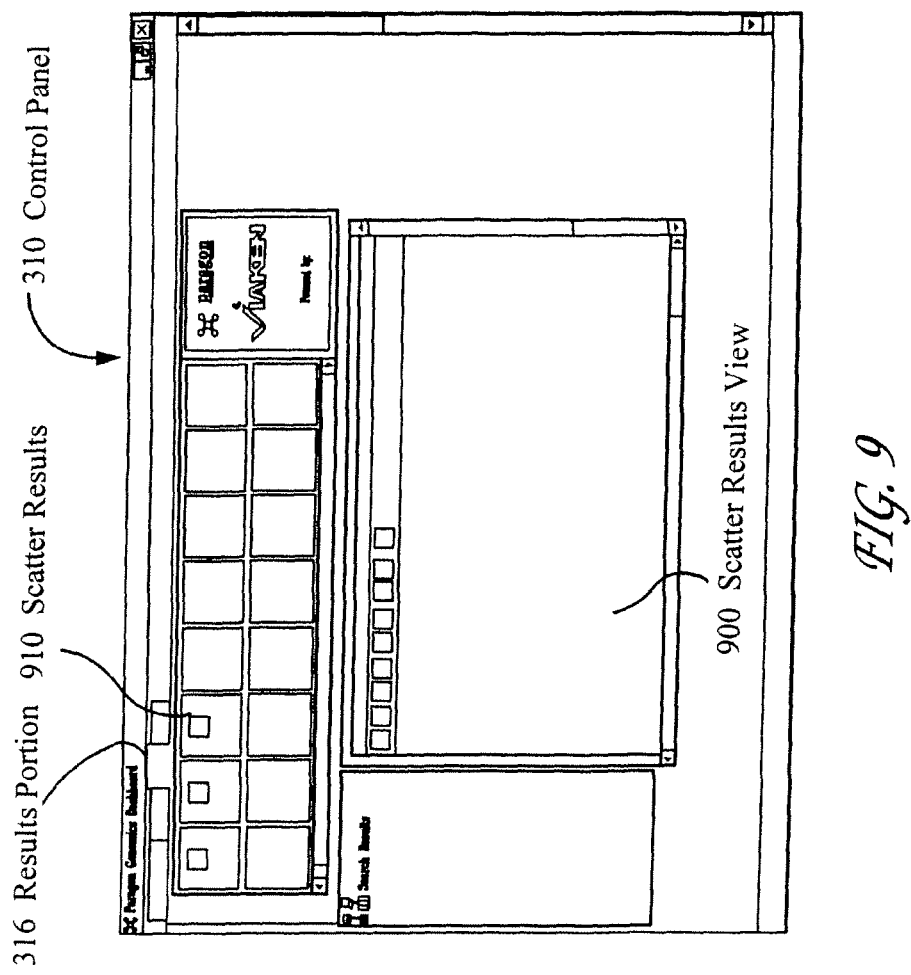
FIG. 9 illustrates a results view associated with scatter results in display panel according to one embodiment of the invention.

FIGS. 7, 8, and 9 illustrate various exemplary results views in accordance with one or more embodiments of the invention. FIG. 7 illustrates a results view 700 associated with cluster results 710 in display panel 730. FIG. 8 illustrates a results view 800 associated with decision results 810 in display panel 730. FIG. 9 illustrates a results view 900 associated with scatter results 910 in display panel 730. These results views 700, 800, 900 are exemplary of the types and views possible in display panel 730. As noted above, virtually any form of view is possible using for example, a browser window within display panel 730. Thus, any suitable type of viewer or display may be used and may vary with the type of result.

In some embodiments of the invention, results portion 316 on control panel 310, when selected may display one or more icons associated with different projects. By selecting one or more of these icons, the user may be afforded the functionality of publishing results sets that may be shared among various users of the bioinformatics system. For example, the user may select a project by name by selecting an icon displayed under results portion 316. This selection may result in the display of a hierarchical folder structure in the display panel. The user may select a folder from the hierarchical folder structure to which they would like to publish results. The user may then highlight in the explorer window the results set that they want to publish and select a "publish" selection portion which may transfer the results to the published results hierarchal structure.

Figure 14:
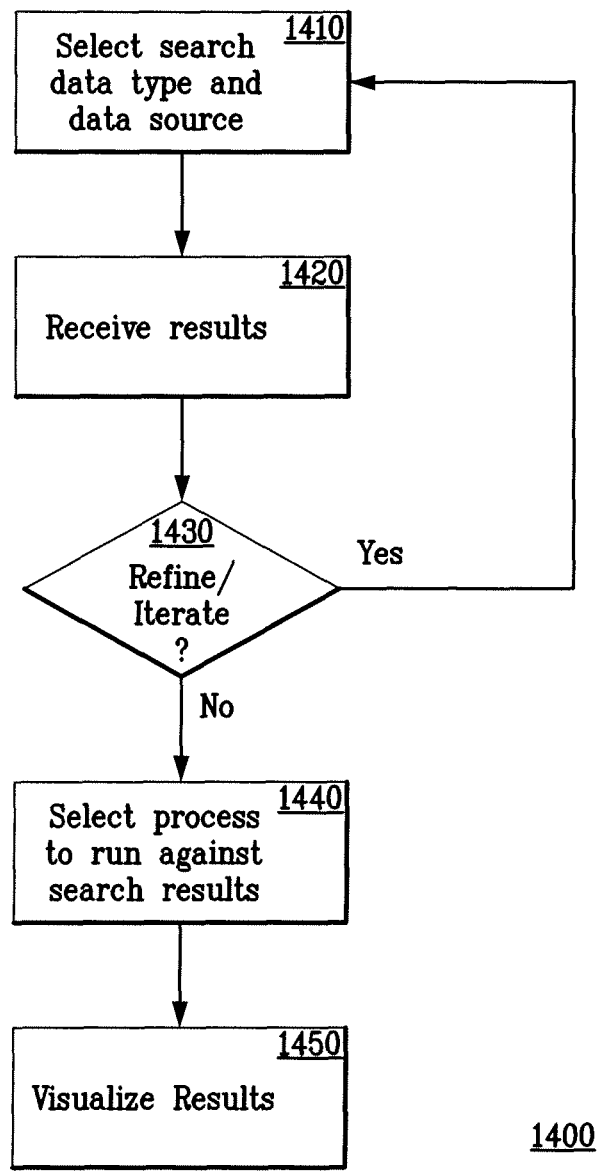
FIG. 14 illustrates an operation of one embodiment of the invention.

FIG. 14 illustrates an operation 1400 of one embodiment of the invention. In an operation 1410, the user selects a type of data to search for along with a data source for that data. In an operation 1420, the search results are received. In an operation 1430, the user may refine the search and/or iterate the search using more or fewer data sources as described above. After the search results are obtained, in an operation 1440, the user selects one or more processes to run against the search results. In an operation 1450, the results of the processed search results are presented to the user.

Bioinformatics system 100 may comprise numerous components that when integrated according to the invention, cooperate to support and achieve the functionality described above. The components may comprise various servers, client devices, data storage devices, and networking devices organized in a variety of manners to address various user needs. For example, a primary delivery platform for the system may be standardized on Sun UltraSparc servers, such as the Sun Enterprise 420r. Secondary supported platforms may include Compaq AlphaServer boxes such as the ES40, and HP boxes such as a J- or L-class server.

Any suitable operating system may be used. For example, the Solaris V7 & V8 on the UltraSparc platform is one possible operating system. Other options for operating systems may include Tru64 Unix V5.1 and Hewlett-Packard HP-UX V11.0 and 11.i.

Any suitable data storage devices may be used. For example, the parts of the system database that are derived from public data sources may access shared storage space on the EMC 8730 SAN. A separate section of the system (e.g. Managed Data Services (MDS)) may be set aside non-public database updates.

Figure 10:
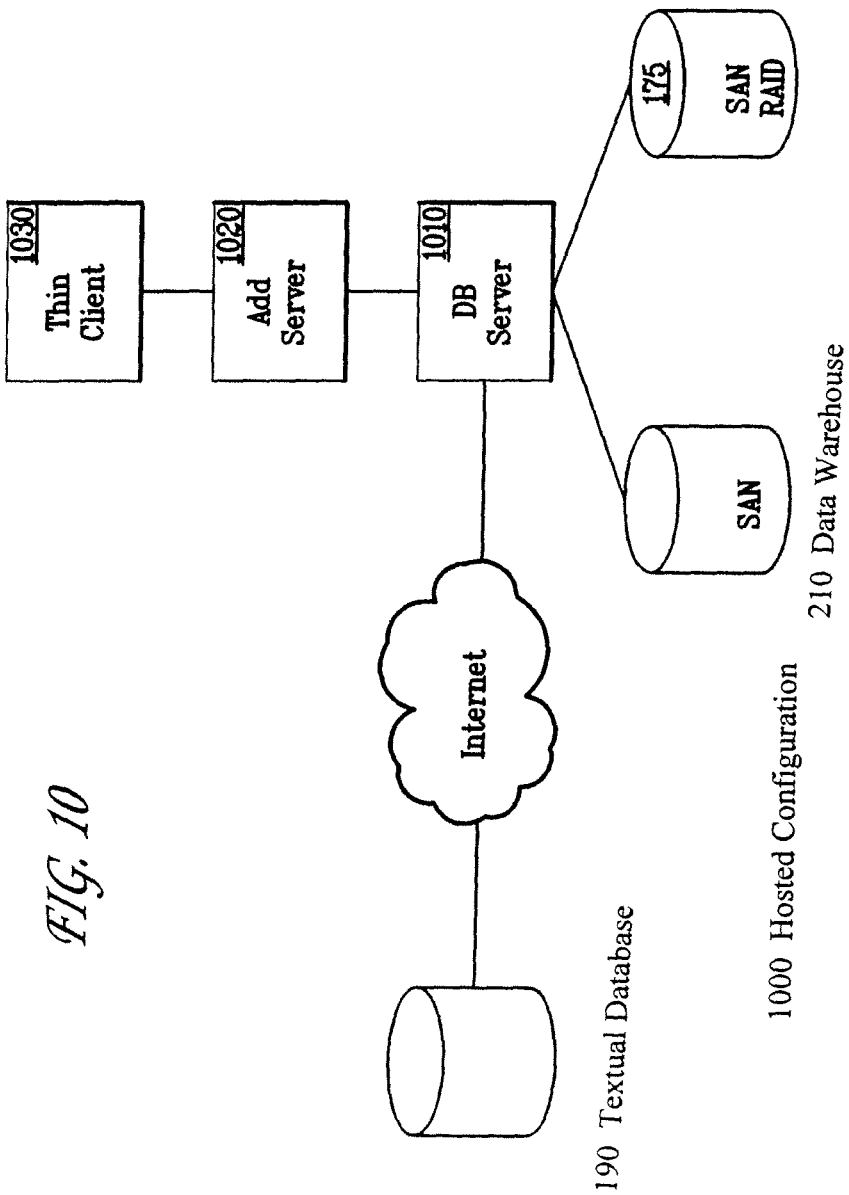
FIG. 10 illustrates an embodiment of the invention in a hosted configuration.
Figure 11:
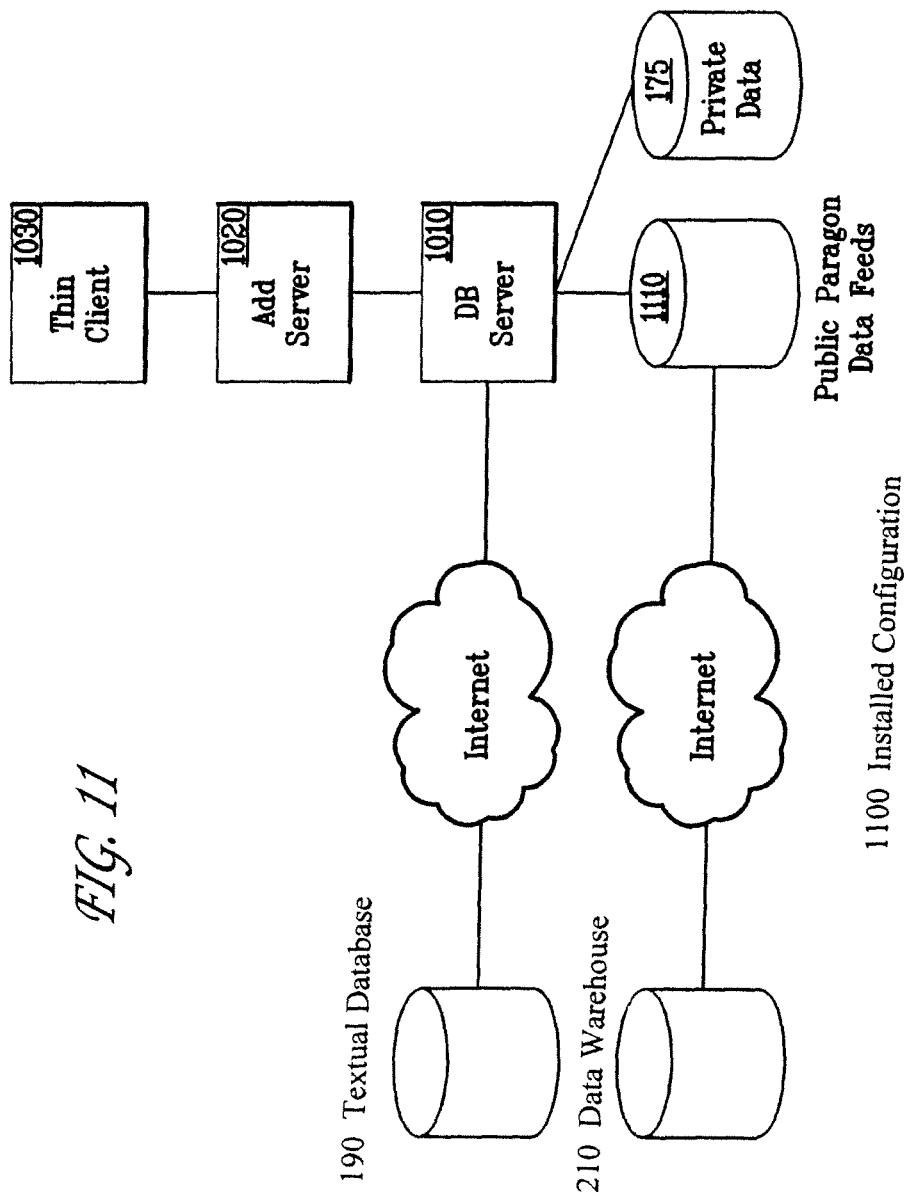
FIG. 11 illustrates an embodiment of the invention in an installed configuration.

FIG. 10 and FIG. 11 illustrate embodiments of the invention useful for implementing various system configurations. FIG. 10 illustrates an embodiment of the invention in a hosted configuration 1000 useful for hosting various aspects of the invention offsite from the user. FIG. 11 illustrates an embodiment of the invention in an installed configuration 1100 useful for implementing various aspects of the invention onsite with the user. Other embodiments may be used as would be apparent.

Hosted configuration 1000 includes a thin client 1030 operable on a user terminal or personal computer, an application server 1020, and a database server 1010. Thin client 1030 operates and/or enables the display of user interface 150. In general, thin clients are generally known. In some embodiments, application server 1020 operates, controls, and/or integrates much of the functionality of the invention. Application server 1020 processes requests obtained from the user through user interface 150 via thin client 1030. This processing may include direct processing on application server 1020 or indirect processing by other processors/servers operating various tasks as would be apparent. Application server 1020 may interface with database server 1010 to process those requests and passes responses back to the user via thin client 1030.

Database server 1010 interfaces with various data sources including private databases 175, unstructured or textual databases 190 (via the Internet) and data warehouse 210. In this configuration, data warehouse 210 is hosted by (or installed at) a service provider separate from the user.

Installed configuration 1100 differs from hosted configuration 1000, namely in that certain aspects of data warehouse 210 are installed at the user whereas other aspects remain at the service provider. Such division of the aspects of data warehouse 210 may by accomplished in various manners dependent upon various business and technical advantages as would be apparent.

The integrated nature of the invention enables certain advantages with respect to overall portfolio management. For example, to continue with the drug development example, various aspects of the invention provide decision support tools that enable intelligent, informed decision making.

Figure 12:
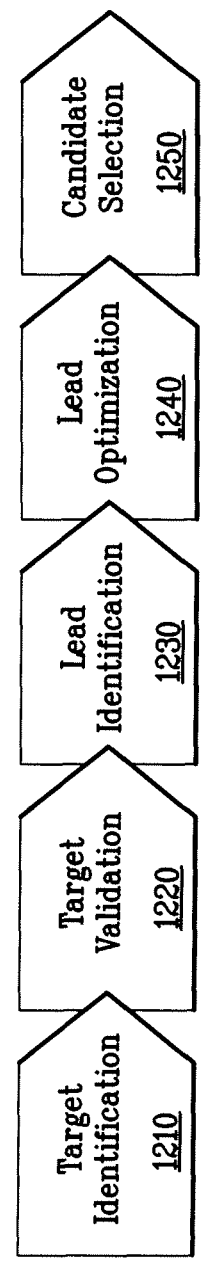
FIG. 12 illustrates various components of a drug discovery process according to one embodiment of the invention.

Some or all aspects of the drug discovery process may be integrated with the invention. For example, as illustrated in FIG. 12, target identification 1210, target validation 1220, lead identification 1230, lead optimization 1240, and candidate selection 1250 may all be evaluated and cross-referenced throughout various aspects of the invention. According to one embodiment of the invention, each of these aspects of the drug discovery process may be implemented in a separate module such as a target identification module, a target validation module, a lead identification module which may or may not be incorporated with a lead optimization module, and a candidate selection module. According to another embodiment of the invention, each of the aspects of the drug discovery process may be implemented in a separate module pertinent to the underlying technical field such as a genomic discovery module, a proteins discovery module, a chemicals discovery module, etc. Furthermore a portfolio management module may oversee various aspects of the overall drug discovery process.

For example, in one embodiment of the invention, the overall drug discovery process may be summarized as follows. One or more genes are identified whose protein products are potentially pivotal intervention points in a specific metabolic or disease process. The genes operate in the cell through various enzymes and structural proteins that they code for. These proteins interact with small molecules in the body or with drug compounds that are introduced in the body to have the ultimate metabolic effects that cause or relieve disease. In terms of the drug discovery process illustrated in FIG. 12, target identification 1210 is focused on identifying the gene, target validation 1220 is focused on identifying the associated protein expressed by the gene, lead identification 1230 and lead optimization 1240 are focused on identifying chemical compounds that cause or relieve the disease.

In another embodiment, target identification 1210 is focused on identifying one or more proteins, and target validation module 1220 is focused on identifying genes associated with the one or more proteins. In another embodiment, target identification 1210 is focused on identifying a gene (e.g., gene for apo-lipoprotein A), and target validation module 1220 is focused on identifying other genes (e.g., gene for apo-lipoprotein B) associated with the gene. In yet another embodiment, target identification 1210 is focused on identifying a protein (e.g. protein for apo-lipoprotein A), and target validation module 1220 is focused on identifying other proteins (e.g. protein for apo-lipoprotein B) associated with the protein.

Thus, according to one aspect of the invention, a target identification module integrates aspects of the invention described herein with a slant toward genomics data. In other words, the target identification module integrates those tools, processes, and viewers, many of which may be known, to search, access, and obtain information associated with gene-related data. This data may include, but is not limited to, EMBL and GeneSeq sequences, Ensembl human genome annotation, KEGG metabolic pathways, NCI-60 gene expression data, LocusLink mapping information along with textual data from Derwent's World Patent Index, and scientific literature from the Web of Science.

According to another aspect of the invention, a target identification module integrates aspects of the invention described herein with a slant toward proteomics data. In other words, the target identification module may integrate tools, processes, and viewers, many of which may be known, to search, access, and obtain information associated with protein-related data. This data may include, but not limited to, protein data from Swiss Prot, Prosite, etc.

According to one aspect of the invention, target validation module integrates aspects of the invention described herein with a slant toward proteomic data. Target validation module is largely focused on validating the genes associated with the disease by determining the exact role of the protein expressed by the genes. In other words, the target validation module integrates those tools, processes, and viewers, many of which may be known, to search, access, and obtain information associated with protein-related data. This data may include, but is not limited to, information about protein sequences, structure, fold, family, motif, protein-protein and protein-ligand interaction data, as well as similar textual data sources as described above.

According to another aspect of the invention, target validation module may integrate aspects of the invention described herein with a slant toward genomic as well as proteomic data. In one embodiment, target validation module may validate the proteins associated with the disease by determining the functions of corresponding genetic determinants, for example, but not limited to other proteins, genes, Quantitative Trait Loci, etc. In another embodiment, target validation module may validate the genes associated with the disease by determining the functions of corresponding genetic determinants, for example, but not limited to other genes, proteins, Quantitative Trait Loci, etc.

According to one aspect of the invention, lead identification module and/or lead optimization module integrate aspects of the invention described herein with a slant toward chemical data. These modules are largely focused on identifying and/or optimizing drugs that correspond to or otherwise interact with genetic determinants including, for example, proteins and genes identified and validated using target identification module and/or target validation module. In other words, these modules integrates those tools, processes, and viewers, many of which may be known, to search, access, and obtain information associated with chemical-related data. This data may include, but is not limited to, information about chemical 1D, 2D and 3D structure and substructure, physiocochemical property, reaction, activity, ADME, and toxicity data as well as similar textual data sources as described above.

Any of the aforementioned modules may operate on its own as a standalone system for processing its associated data. In some embodiments of the invention, various one of the modules operate cooperatively with one another. In other embodiments of the invention, each of the modules operates cooperatively with one another to transform the conventional drug discovery process and advantageously achieve various aspects of the invention.

In this manner, a portfolio manager module may, at any time, be able to call up information regarding the projected cost and benefits of research for a particular drug discovery program. For example, a manager may wish to evaluate potential costs of new drug discovery programs in view of revenue from a drug that is in the latter stages of a regulatory approval process. The aspects of the invention enable the manager to evaluate this, and other, data and make an informed decision.

One advantage of the invention is the ability to provide life scientists with access to the right information at the right time at their desktop via an intuitive user interface, thus allowing the life scientists to analyze, share, and report the information easily.

Another advantage provided by the invention is the ability to accelerate accurate decision making by providing an intuitive user interface for life scientists that has the necessary tools and information.

Yet another advantage of the invention is the ability to enhance research productivity by providing an intuitive user interface that facilitates access to automated analysis and report generation tools.

Still yet another advantage provided by the invention is the ability to improve information flow by removing information bottlenecks.

Another advantage of the invention is the facilitation of multidisciplinary project team information sharing.

Other embodiments, uses and advantages of the invention will be apparent to those skilled in the art from consideration of the specification and practice of the invention disclosed herein. The specification should be considered exemplary only.

What is claimed:

1. A computer-implemented bioinformatics system comprising: a user interface hardware module for receiving a search query from a user and for providing processed results to the user, wherein the search query comprises user selected data type information, user selected data source information, and user specified query parameters, in addition to the data type and data source information; and
   an application host that interfaces said user interface hardware module with:
   a search engine module that searches a structured database and an unstructured database using said search query to obtain search results, and
   a plurality of informatics tools at least one of which processes said search results to provide processed results.

2. A computer-implemented bioinformatics research system comprising:
   a computer comprising a computer operating system; the computer further comprising
   a user interface hardware module configured to receive a search query from a user, wherein the search query comprises user selected data type information, user selected data source information, and user specified query parameters, in addition to the data type and data source information;
   a search engine module configured to receive the search query from the user interface hardware module, conduct a search of data from multiple data sources based on the search query, and generate search results based on the search;
   the user interface hardware module further comprising;
   a display module, configured to receive the search results and generate a display based on the search results,
   a module to receive from a user, selection of an informatics tool to be used to further process the search results;
   a process module configured to process said search results to provide processed results; and
   means for displaying the processed search results.

3. The system of claim 2, wherein the user interface hardware module further comprises a data type selection object for enabling a user to select from among various available types of data to be used for a search query.

4. The system of claim 2, wherein the user interface hardware module further comprises a data source display component for displaying options for a user to select from among a number of data sources and a selection mechanism for enabling a user to select, for a search query, the data sources to be searched.

5. The system of claim 2, wherein the user interface hardware module further comprises a data type selection object for enabling a user to select at least one data type from among various available types of data, a data source display component for displaying options for a user to select from among a number of data sources corresponding to a selected data type and a data source selection mechanism for enabling a user to select, for a search query, the data sources to be searched.

6. The system of claim 2, wherein the user interface hardware module further comprises a data type selection object for enabling a user to select at least one data type from among various available types of data, a data source display component for displaying options for a user to select from among a number of data sources corresponding to a selected data type and a data source selection mechanism for enabling a user to select, for a search query, the data sources to be searched, wherein the data sources include private and public data sources.

7. The system of claim 2, wherein the user interface hardware module further comprises a data type selection object for enabling a user to select from among various available types of data and a search dialog display component for displaying a search dialog for a selected data type.

8. The system of claim 2, wherein the user interface hardware module further comprises a data type selection object for enabling a user to select from among various available types of data and a search dialog display component for displaying a search dialog specific to a selected data source.

9. The system of claim 2, wherein the user interface hardware module further comprises a search type selection mechanism for enabling a user to select how a data source is to be queried.

10. The system of claim 2, wherein the user interface hardware module further comprises a probabilistic text search selection mechanism for enabling a user to select a probabilistic text search.

11. The system of claim 2, wherein the user interface hardware module further comprises a relevance selection mechanism for enabling the user to specify a relevance criteria to be used in a search.

12. The system of claim 2, wherein the user interface hardware module further comprises a search results selection mechanism for enabling a user to select various ones of displayed searched results for further processing.

13. The system of claim 2, wherein displayed search results include an indication of a data source from which a search result was obtained.

14. The system of claim 2, wherein the user interface hardware module further comprises a process selection object for displaying, along with a search result, a representation of types of processes that can be run against the search result.

15. The system of claim 2, wherein the user interface hardware module further comprises a process selection indicator for displaying, along with a search result, a representation of types of processes that can be run against the search result, the processes including an iterative search process for enabling a user to select an iterative search for selected search results.

16. The system of claim 15, wherein the process includes a business process selection mechanism.

17. The system of claim 15, wherein the process includes a research process selection mechanism.

18. The system of claim 15, wherein the displayed processes are limited to the types of processes relevant to the type of data in the search results.

19. The system of claim 2, wherein the user interface hardware module further comprises a process selection indicator for displaying, along with a search result, a representation of types of processes that can be run against the search result, the processes including an iterative search process for enabling a user to select an iterative search for selected search results, and wherein the user interface hardware module further comprises a data source display object for displaying, in response to a user selecting an iterative search option, one or more of:

a data source selection mechanism for selecting among a number of data sources against which the iterative query is to be run; or a data type selection mechanism and a relevance selection mechanism.

20. The system of claim 2, wherein the user interface hardware module further comprises means for enabling a user to create an informatics workflow and save an icon associated with the workflow.

21. The system of claim 2, wherein the user interface hardware module further comprises means for enabling a user to select a process to be performed on selected data and means for receiving the results of the selected processing.

22. The system of claim 2, wherein the user interface hardware module further comprises means for enabling a user to select a process to be performed on selected search results data and means for automatically displaying the results of the selected processing in the display.

* * * * *